(12) United States Patent
Nazareth et al.

(10) Patent No.: US 8,802,427 B2
(45) Date of Patent: Aug. 12, 2014

(54) FEMALE FERTILITY TEST

(75) Inventors: Albert R. Nazareth, Mercerville, NJ (US); Timothy Snowden, Howell, NJ (US); Mary Beth Boyle, Pennington, NJ (US); Shang Li, West Windsor, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 710 days.

(21) Appl. No.: 12/480,882

(22) Filed: Jun. 9, 2009

(65) Prior Publication Data

US 2010/0311188 A1 Dec. 9, 2010

(51) Int. Cl.
*C12M 1/34* (2006.01)
*C12Q 1/04* (2006.01)

(52) U.S. Cl.
CPC .............. *C12Q 1/04* (2013.01); *Y10S 435/805* (2013.01); *Y10S 435/81* (2013.01); *Y10S 435/97* (2013.01)
USPC ........ 435/287.7; 422/401; 422/420; 422/425; 422/430; 435/287.9; 435/805; 435/810; 435/970

(58) Field of Classification Search
CPC .......................... G01N 33/558; G01N 2333/59
See application file for complete search history.

(56) References Cited

U.S. PATENT DOCUMENTS

| | | | |
|---|---|---|---|
| 4,313,734 A | 2/1982 | Leuvering | |
| 4,366,241 A | 12/1982 | Tom et al. | |
| 4,859,612 A | 8/1989 | Cole et al. | |
| 5,141,850 A | 8/1992 | Cole et al. | |
| 5,521,102 A * | 5/1996 | Boehringer et al. | 436/523 |
| 5,602,040 A * | 2/1997 | May et al. | 436/514 |
| 5,739,041 A | 4/1998 | Nazareth et al. | |
| 5,846,835 A | 12/1998 | Sisbarro et al. | |
| 5,985,675 A * | 11/1999 | Charm et al. | 436/514 |
| 6,319,676 B1 | 11/2001 | Nazareth et al. | |
| 6,485,982 B1 | 11/2002 | Charlton | |
| 7,045,342 B2 | 5/2006 | Nazareth et al. | |
| 7,326,578 B2 | 2/2008 | Bateman et al. | |
| 2012/0083047 A1 * | 4/2012 | Nazareth et al. | 436/501 |

OTHER PUBLICATIONS

Vermes et al, "Interpretations of Five Monoclonal Immunoassays of Lutropin and Follitropin: Effects of Normalization with WHO Standard", Clin. Chem., 37/3, 415-421, 1991.*
Frens, "Controlled Nucleation for the Regulation of the Paraticle Size in Monodisperse Gold Suspensions," Nature, *Physical Science*, 1973, pp. 20-22, vol. 241.
Horisberger, Evaluation of Colloidal Gold as a Cytochemical Marker for Transmission and Scanning Electron Microscopy, *Bio. Cellulaire*, 1979, pp. 253-258, vol. 36.
Leuvering et al., "Sol Particle Immunoassay," *J. Immunoassay*, 1980, pp. 77-91, vol. 1, No. 1.
Tijssen, "Practice and Theory of Enzyme immunoassays; The Immunoreactants on Solid Phases", *Laboratory Techniques in Biochemistry and Molecular Biology*, Chapter 13, pp. 297-328, vol. 15, 1985.

* cited by examiner

*Primary Examiner* — Chris L Chin
(74) *Attorney, Agent, or Firm* — Ryan W. Cagle; Stephen B. Shear

(57) ABSTRACT

The present invention is related to a diagnostic test kit that assesses ovarian reserve by measuring Follicle Stimulating Hormone (FSH) in a liquid sample. The sample can be deposited on a first portion of the device for transport to a second portion of the device. The device can include a release medium formed of a first material and including a detectable label thereon and a capture medium, including a test site, in fluid communication with the release medium and formed of a second, different material.

3 Claims, 10 Drawing Sheets

FEMALE FERTILITY TEST

FIELD OF THE INVENTION

The present invention is related to devices for testing ovarian reserve in pre- and peri-menopausal women.

BACKGROUND OF THE INVENTION

Many women do not realize that a significant decline in fertility begins in the early 30's. In fact, for many successful fertility treatments, the predominate predictor of pregnancy outcome is the age of the female partner. The significant impact that age has on fertility is related to both the quality and quantity of a woman's eggs.

Women are born with all the eggs that they will ever have. As such, the ovary can be generally thought of as an egg bank from which a woman withdraws during her reproductive life. Each month one egg or more is released during ovulation, but about one thousand additional eggs are lost by follicular atresia. Thus, with advanced maternal age the number of eggs that can be successfully recruited for a possible pregnancy declines.

In addition to this decrease in the number of eggs that women experience, some women may have poor quality eggs that reduce the likelihood that a given fertility treatment will result in a healthy pregnancy. Ovarian reserve screening is one mechanism by which fertility specialists can partially predict the reproductive potential of a specific patient as well as the potential of her eggs to result in a healthy pregnancy. Ovarian reserve is the term typically used to define the capacity of the ovary to provide eggs that are capable of fertilization. As such, the determination of a woman's ovarian reserve is an important aspect in the management and treatment of infertility.

Assessing ovarian reserve is routinely conducted for determining infertility in women of advanced reproductive age. One of the key indicators to determine the reproductive potential in women is the basal Follicle Stimulating Hormone (FSH) level on days 2-5 of the menstrual cycle. Elevated FSH at the early follicular phase is indicative of diminished ovarian reserve. Currently, the most common test for assessing ovarian reserve is the day 3 FSH test. This blood test determines the level of FSH on cycle day 3. Cycle day 3 is chosen because at this time the estrogen level is expected to be low, a critical feature, as FSH levels are subject to a negative feedback. Generally FSH levels are expected to be below 10 mIU/ml in women with reproductive potential (e.g., levels of 10-15 mIU/ml are considered borderline).

While measuring serum FSH is still the standard practice and widely adopted in fertility clinics, such testing is not well suited for home use by an individual. As such, there remains a need for a reliable and more convenient and cost effective diagnostic test for home use, such as an over the counter test.

BRIEF SUMMARY OF THE INVENTION

The present invention satisfies at least some of the aforementioned needs by providing a diagnostic test kit that assesses ovarian reserve by assessing Follicle Stimulating Hormone (FSH) in urine, preferably Day 3 first morning urine. Embodiments of the present invention comprise a device for detecting FSH in a liquid sample deposited preferably on a sample absorbent in contact with a first portion of the device for transport to a second portion of the device, such as a lateral flow platform. These embodiments can include a release medium formed of a first material, such as Ahlstrom 989, and a labeled conjugate comprising a detectable label and a first binding member reactive with a first epitope of FSH. The release medium also can include a biotinylated capturable component having a second binding member reactive with a second epitope of FSH. In such embodiments, if FSH is present in the sample a complex is formed between the labeled conjugate, FSH, and the biotinylated capturable component. These embodiments also can include a capture medium in fluid communication with the release medium. The capture medium is formed of a different material, such as nitrocellulose, than the release medium. The capture medium can include a test site having immobilized thereon a capture component. The capture component in these embodiments is capable of binding with the biotinylated capturable component.

Accordingly, a liquid sample applied to the release medium at a sample deposit location positioned upstream of both the labeled conjugate and the biotinylated capturable component wicks downstream past the labeled conjugate and the biotinylated capturable component (not necessarily in this order). If the sample includes any FSH, then a sandwich complex is formed between the labeled conjugate, FSH, and the biotinylated capturable component. As the liquid sample front travels from the release medium onto the capture medium, the complex is carried across the capture medium until it reaches the test site, which includes an immobilized binding member reactive with the biotinylated capturable component. When FSH is in the sample, the labeled complex (i.e., labeled conjugate-FSH-biotinylated capturable component) is bound and capable of being detected at the test site.

In other embodiments, the present invention provides a device for detecting FSH in a liquid sample at a concentration relative to a predetermined level. In certain embodiments, the predetermined amount or level of FSH can be referred to as a threshold amount of FSH. Particularly, the predetermined level can refer to FSH at a concentration that is deemed to be an elevated level. Preferred embodiments include a sample application member for receiving the liquid sample and a first portion (e.g., a release medium) including a labeled conjugate with a detectable label and a first binding member reactive with a first epitope of FSH. The labeled conjugate is preferably present in excess relative to an amount of labeled conjugate necessary to bind the FSH present at the predetermined level. The device also includes a second portion including a test site having immobilized thereon a capture component capable of directly or indirectly binding FSH bound to the labeled conjugate and a reference site having immobilized thereon a capture component comprising a binding member that binds a portion of the excess amount of the labeled conjugate. The device can also include a reservoir for containing liquid sample and excess labeled conjugate not captured at the test site and the reference site. In such embodiments, the color intensity of the reference site is calibrated to be inversely proportional to the concentration of FSH present in the sample. Assessment of the FSH level in the sample is based on the comparison of resulting color intensities at the test site and reference site.

In certain embodiments, the present invention provides a device for detecting FSH present in a liquid sample at a concentration relative to a predetermined level. The device can include a sample application member for receiving the liquid sample, a first portion including a labeled conjugate with a detectable label and a first binding member reactive with a first epitope of FSH, and a second portion including a single test site having immobilized thereon a capture component capable of directly or indirectly binding FSH. In such embodiments, the device can be calibrated such that a signal (e.g., color development) indicating binding of FSH at the test site only occurs when FSH is present in the liquid sample at a concentration above the predetermined level and no signal at the test site indicates any FSH in the liquid sample is present at a concentration below the predetermined level.

In other embodiments, the present invention provides a device for detecting FSH in a liquid sample by utilizing a scavenger component. In such embodiments, the device includes a release medium formed of a first material and including a detectable label as well as a capture medium in fluid communication with the release medium. The capture medium is preferably formed of a different material than that of the release medium. The capture medium includes a test site. However, these embodiments also include a scavenger component that is reactive with any of the following: (i) FSH, (ii) a FSH-labeled conjugate complex, (iii) a biotinylated capturable component-FSH-labeled conjugate complex, or (iv) combinations of (i) through (iii). The scavenger component can be located anywhere between the location of sample deposit and the test site.

In preferred embodiments, the scavenger component is provided in an amount to bind with a specific amount of FSH. As such, any amount of FSH above the predetermined level in the sample will be bound to the labeled conjugate and detected at the test site. That is, the specific amount of FSH can be substantially equal to the predetermined level of FSH. The specific amount of FSH to be bound by the scavenger component can be calibrated to correlate with a given concentration to reflect the predetermined level of FSH in the sample. That is, samples having an FSH concentration exceeding the predetermined level will bind with the labeled conjugate and be captured at the test site.

In another embodiment, a device according to the invention for detecting FSH present in a liquid sample at a concentration relative to a predetermined level can be designed to provide a single site or line for reading by a user to determine whether FSH levels are normal or elevated. Specifically, the single line can be a test site, and the device can be designed such that the formation of a signal at the test site indicates FSH values are elevated and the lack of formation at the test site indicates that FSH values are normal. In some embodiments, to indicate to the user that the device is functional (even though no signal is detected at the test site—meaning FSH values are normal), the device may include a control line wherein the presence of a signal is independent of normal or elevated FSH values and solely indicates that the device is functional.

Specifically, a device according to this embodiment of the invention may include a sample application member for receiving the liquid sample; a first portion comprising a labeled conjugate with a detectable label and a first binding member reactive with a first epitope of FSH; and a second portion comprising a single test site having immobilized thereon a capture component capable of directly or indirectly binding FSH. Preferably, the device is calibrated such that a signal indicating binding of FSH at the test site only occurs when FSH is present in the liquid sample at a concentration above the predetermined level and no signal at the test site indicates any FSH in the liquid sample is present at a concentration below the predetermined level. Preferably, the single test site is the only site on the device visible to a user for indicating FSH concentration in the liquid sample.

In the above embodiments, calibration can comprise the use of a scavenger component, which can be located between the sample application member and the test site. Preferably, the scavenger component will bind any FSH present in the sample below the predetermined level. Of course, other means could be used for such calibration.

In another aspect, the present invention provides a method of determining ovarian reserve utilizing a test device according to embodiments of the present invention. In one embodiment, a liquid sample is applied to a sample deposit location positioned upstream of a labeled conjugate and the biotinylated capturable component located on the release medium. The liquid sample travels downstream from the sample deposit location and passes through a site including the labeled conjugate and a site including the biotinylated capturable component. The resulting complex is captured at the test site. The labeled conjugate is detected and signals the presence of FSH. Depending on the concentration of FSH in the sample, the resulting color intensity at the test site will vary.

In preferred embodiments, the capture medium of the test device also includes a reference site having immobilized thereon a binding member reactive with the labeled conjugate. Preferably, the reference site is "active" in the sense that the resulting color intensity changes based on the concentration of FSH in the sample. Specifically, the color intensity at the reference site can be inverse to the concentration of FSH present in the liquid sample. For instance, as FSH concentrations increase, more of the labeled conjugate is complexed with FSH and the biotinylated capturable component and captured at the test site. As a result, less labeled conjugate is available to flow past the test site and bound at the reference site. Accordingly, a woman's ovarian reserve can be determined based by a color comparison or "color matching" of the reference site and the test site. This also may be described as intensity matching or a comparison of the color intensity at the reference site versus the color intensity at the test site.

Preferably, the color intensity of the reference site is calibrated to correlate with the color intensity at the test site. For example, a predetermined level of FSH (e.g., lowest concentration deemed as being elevated) can be selected and an amount of labeled conjugate can be applied to the release medium so that if a sample contains the predetermined level of FSH then a portion of the labeled conjugate will bind the FSH and be captured at the test site while the remainder of the labeled conjugate will pass the test site and a portion will bind at the reference site, with any excess labeled conjugate flowing past the reference site. In such a case, color intensity at the test site and the reference site should be practically equal and signal that the sample contained the predetermined level of FSH. In the event that the sample has an FSH concentration above the predetermined level, the color intensity of the reference site will be lighter than the color intensity of the test site, thus indicating that the FSH concentration of the sample was elevated. If the color intensity of the reference site is darker than that of the test site, then the FSH concentration of the sample was normal.

BRIEF DESCRIPTION OF THE SEVERAL VIEWS OF THE DRAWINGS

Figure 1A:
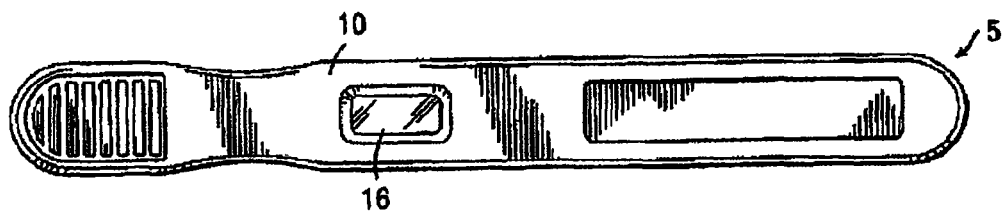
Figure 1B:
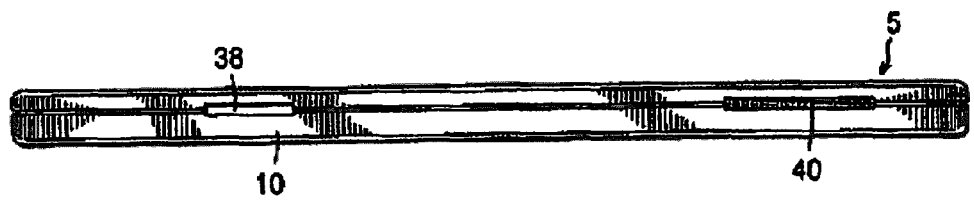
Figure 1C:
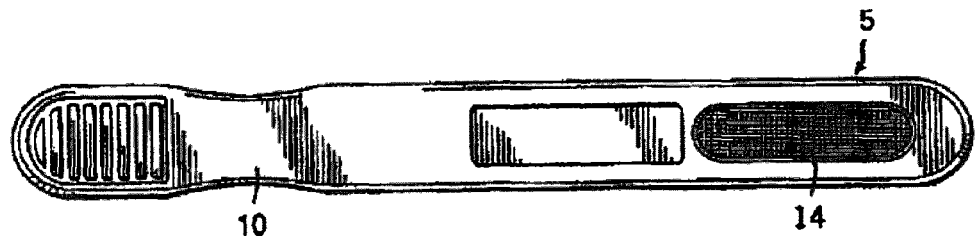
Figure 1D:
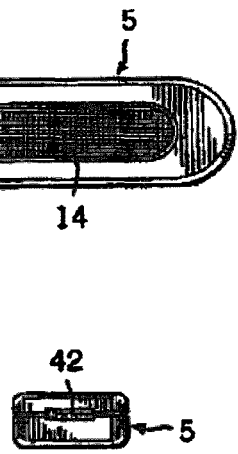
Figure 1E:
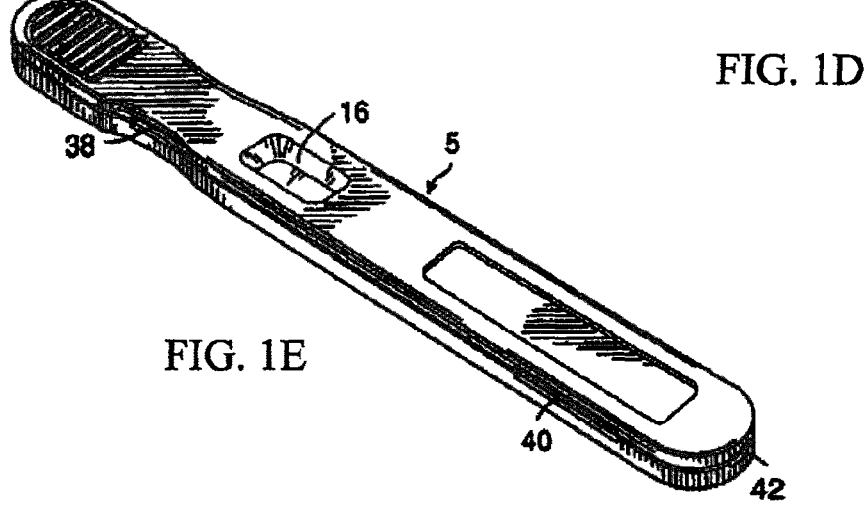
Figure 2A:
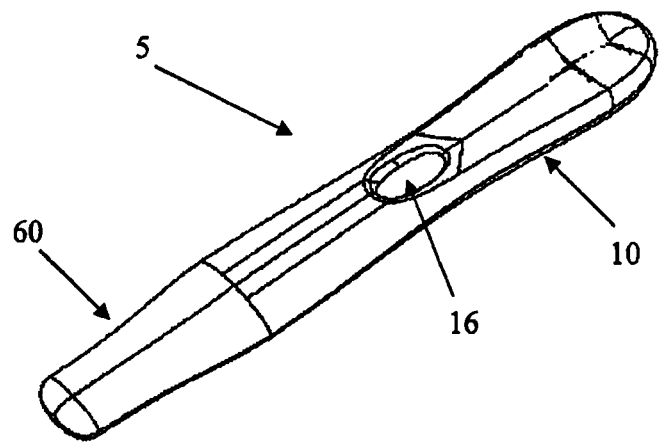
Figure 2B:
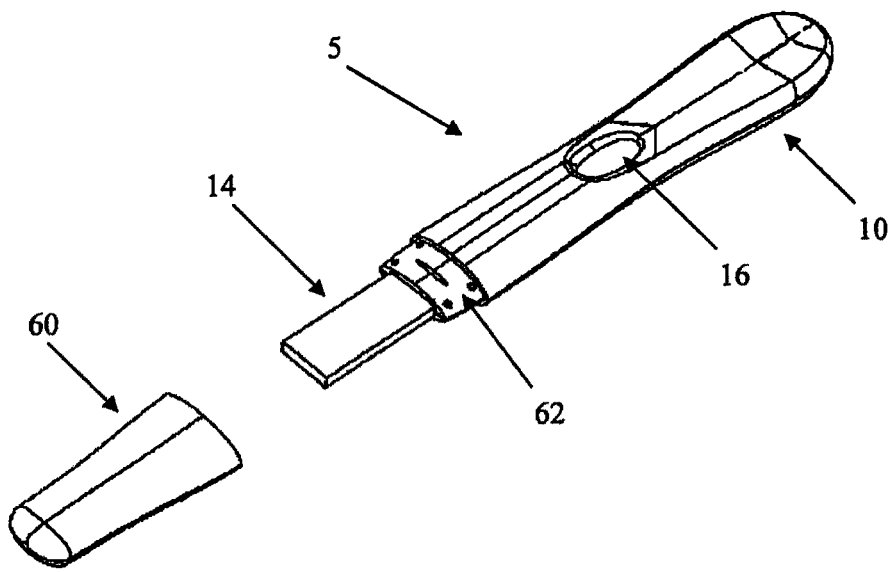
Figure 2C:
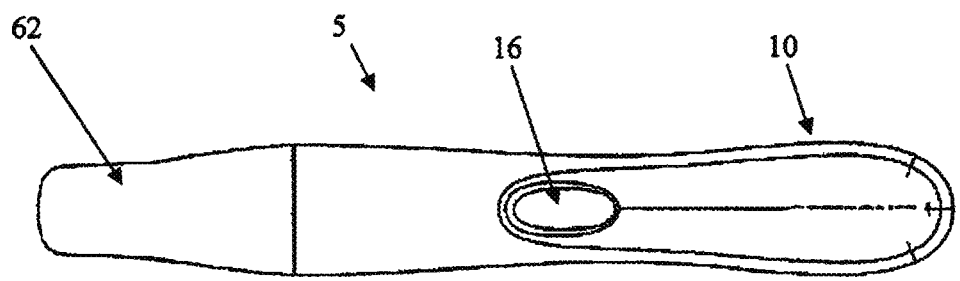

Having thus described the invention in general terms, reference will now be made to the accompanying drawings, which are not necessarily drawn to scale, and wherein:

FIG. 1A depicts a top view of one embodiment of a test device according to the present invention;

FIG. 1B depicts a longitudinal side view of an embodiment of a test device according to the present invention;

FIG. 1C depicts a bottom view of an embodiment of a test device according to the present invention;

FIG. 1D depicts a tail end view of an embodiment of a test device according to the present invention FIG. 1E depicts a top perspective view an embodiment of a test device according to the present invention;

FIG. 2A depicts a front, top, left side perspective view of a preferred embodiment of a test device according to the present invention;

FIG. 2B depicts the test device according to the embodiment from FIG. 2A with the cap thereof removed;

FIG. 2C depicts a top plan view of the test device embodiment from FIG. 2A

Figure 2D:
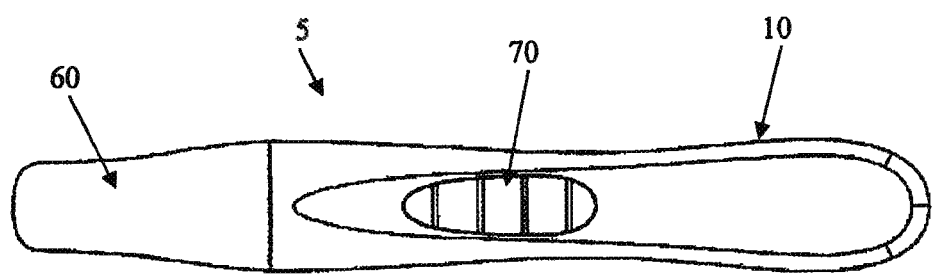

FIG. 2D depicts a bottom plan view of the test device embodiment from FIG. 2A

Figure 2E:
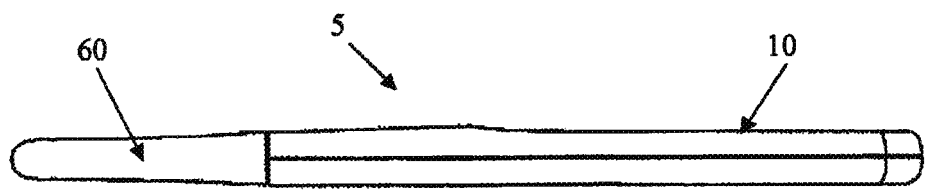
Figure 3:
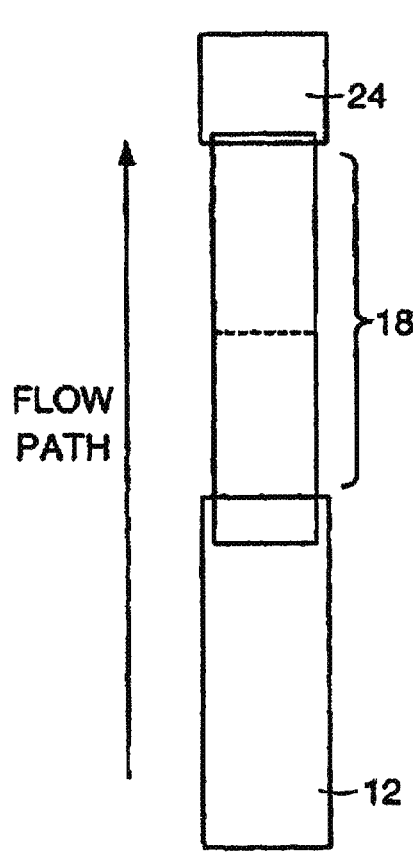
Figure 4:
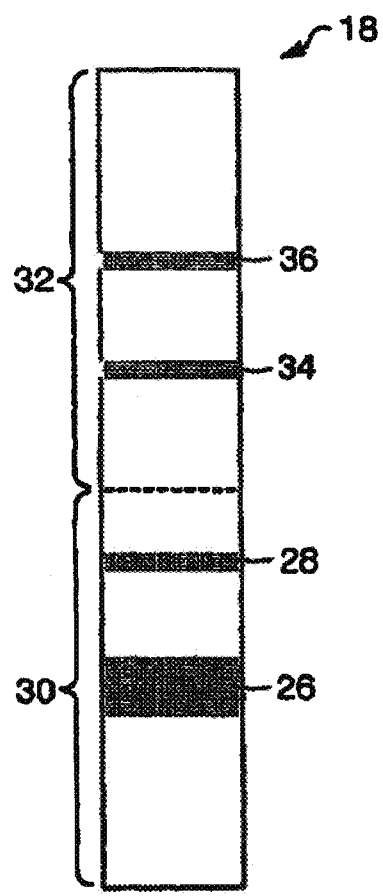
Figure 5:
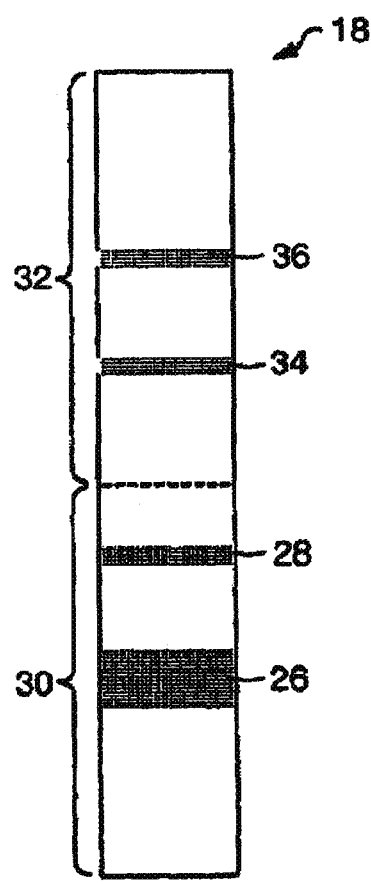
Figure 6:
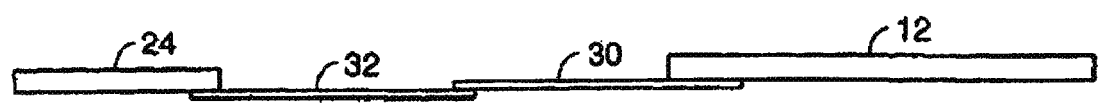
Figure 7A:
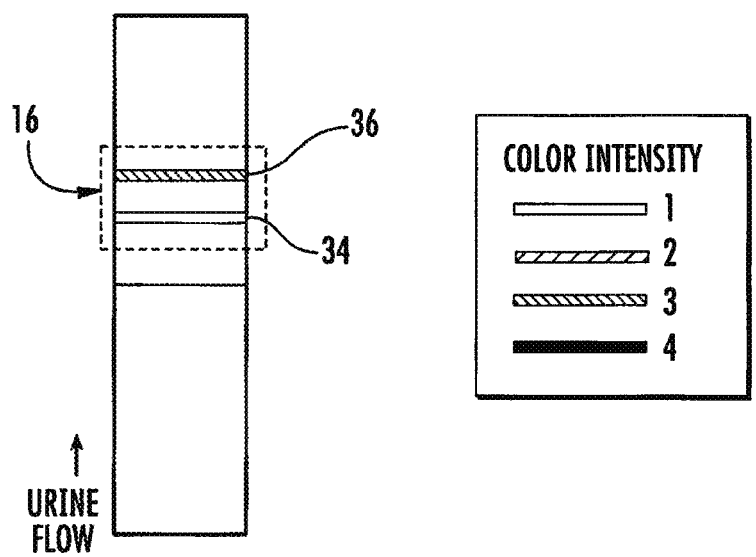
Figure 7B:
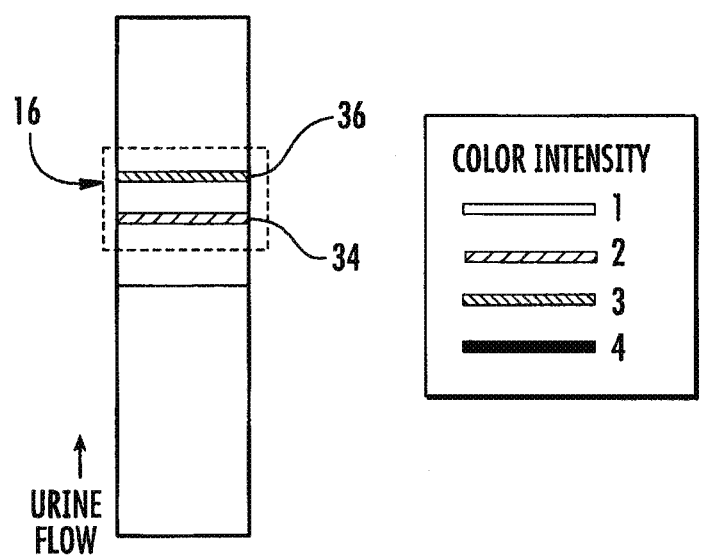
Figure 7C:
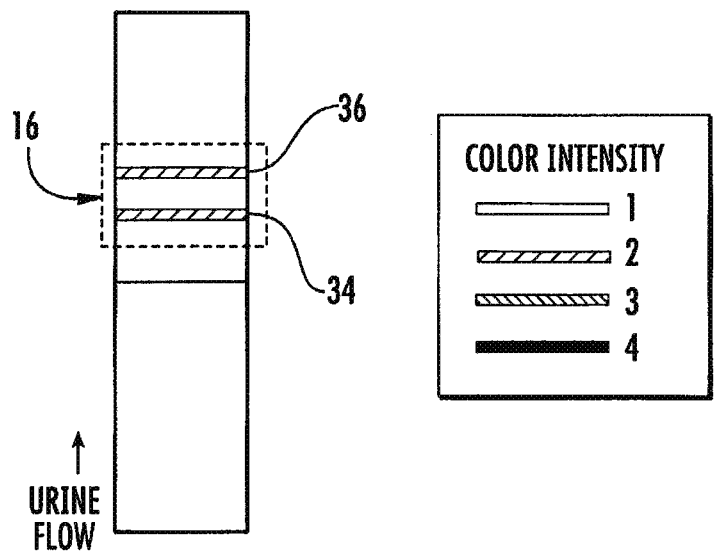
Figure 7D:
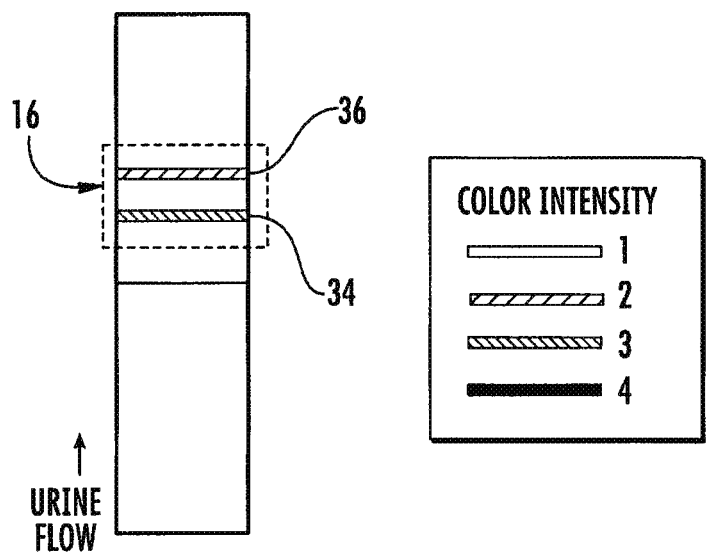
Figure 8A:
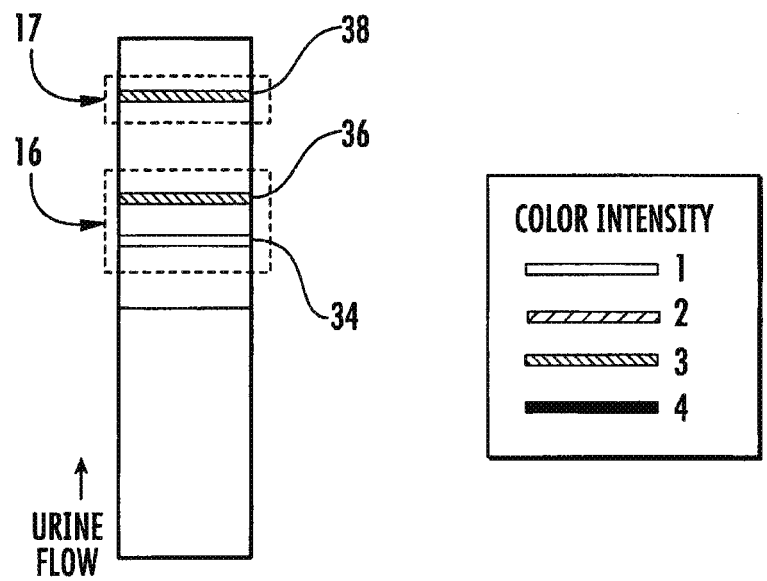
Figure 8B:
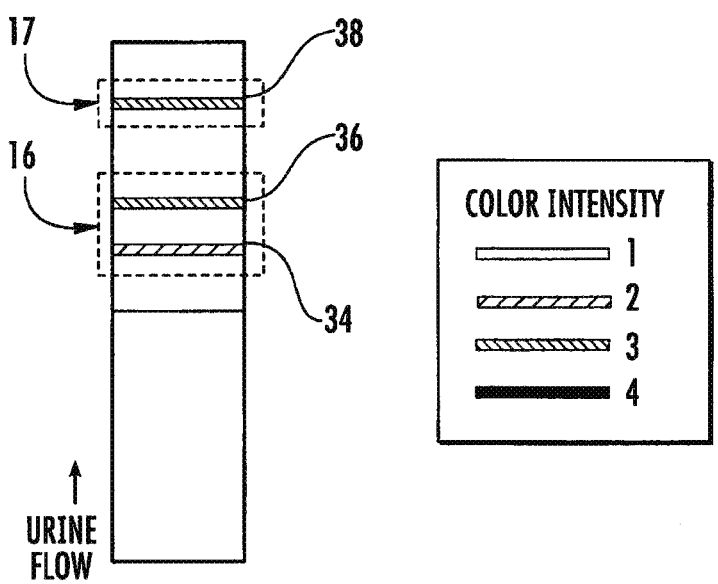
Figure 8C:
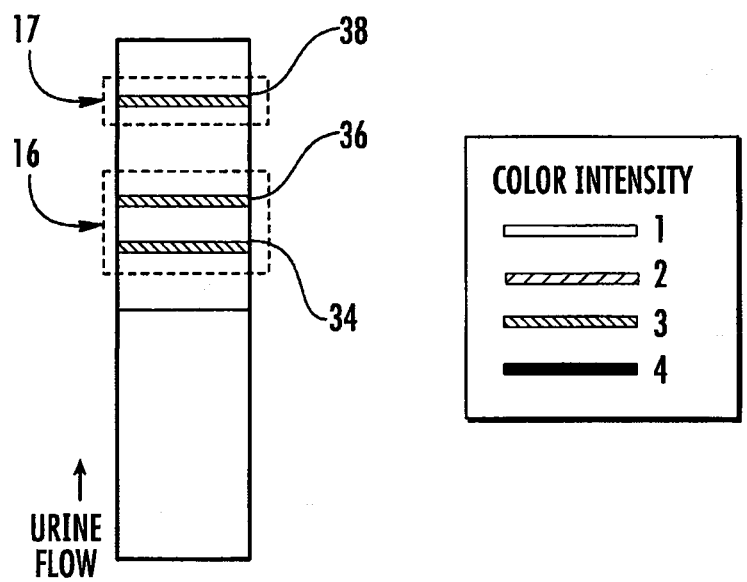
Figure 8D:
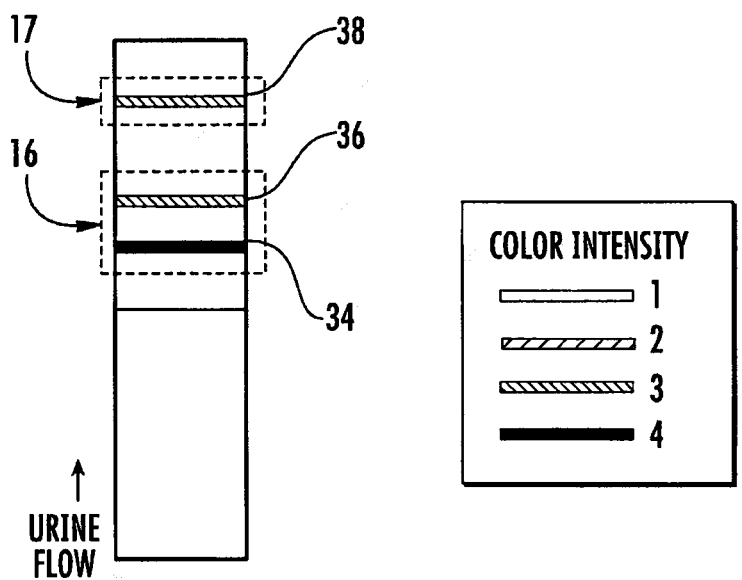
Figure 9:
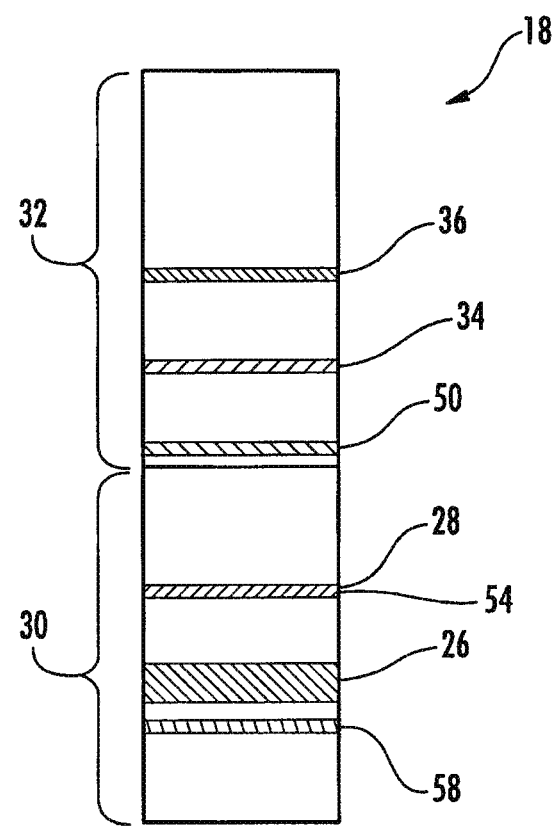

FIG. 2E depicts a left side elevational view of the test device embodiment from FIG. 2A;

FIG. 3 depicts a schematic top view of a biphasic substrate according to one embodiment of the invention;

FIG. 4 depicts a schematic top view of a biphasic substrate according to one embodiment of the invention;

FIG. 5 depicts a schematic top view of a biphasic substrate according to another embodiment of the invention;

FIG. 6 depicts a schematic side view of the embodiment of a test device according to the invention illustrated in FIGS. 2A-2C;

FIG. 7A depicts a color matching result that indicates a normal level of FSH according to one embodiment of the invention;

FIG. 7B depicts another color matching result that indicates a normal level of FSH according to one embodiment of the invention;

FIG. 7C depicts a color matching result that indicates an elevated level of FSH according to one embodiment of the invention;

FIG. 7D depicts another color matching result that indicates an elevated level of FSH according to one embodiment of the invention;

FIG. 8A depicts one embodiment of the invention having a control site and illustrating a color matching result that indicates a normal level of FSH;

FIG. 8B depicts another embodiment of the invention having a control site and illustrating a color matching result that indicates a normal level of FSH;

FIG. 8C depicts one embodiment of the invention having a control site and illustrating a color matching result that indicates an elevated level of FSH; and FIG. 8D depicts another embodiment of the invention having a control site and illustrating a color matching result that indicates an elevated level of FSH FIG. 9 illustrates a few possible locations for striping a scavenger component onto test devices according to certain embodiments of the present invention.

DETAILED DESCRIPTION OF THE INVENTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In one aspect, the present invention provides a fertility test device, such as an OTC or POC fertility test, that can determine ovarian reserve. In certain embodiments, a liquid sample can preferably be deposited via a sample application member on a first portion of the device for transport to a second portion of the device that is in fluid contact with the first portion. In general terms, the device according to various embodiments includes a first binding member located in the first portion of the device and a second binding member located in the second portion of the device. Such devices include a test site located in the second portion of the device that directly or indirectly binds the FSH. The presence of FSH in the liquid sample can be determined by visual inspection of the test site, preferably by comparing the relative presence of color development at the capture and reference sites caused by the direct or indirect binding of FSH at the test site.

As used herein, "antibody" refers to a polypeptide substantially encoded by an immunoglobulin gene or immunoglobulin genes, or fragments thereof, which specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. The term "antibody," as used herein, also includes antibody fragments either produced by the modification of whole antibodies or those synthesized de novo using recombinant DNA methodologies, and further includes "humanized" antibodies made by now conventional techniques.

As used herein, a "capture antibody" should be understood as an antibody, such as a monoclonal or polyclonal antibody, attached to a substrate, such as a solid substrate. The capture antibody can include at least one binding member that specifically binds a particular, distinct epitope of an antigen, such as FSH. Embodiments of the present invention preferably make use of a conjugate comprising an antibody bound to a detectable label component (which can specifically be colored particles, such as a metal sol or colloid, preferably gold).

Any detectable label recognized in the art as being useful in various assays could be used in the present invention. In particular, the detectable label component can include compositions detectable by spectroscopic, photochemical, biochemical, immunochemical, or chemical means. The label component thus produces a detectable signal. Exemplary labels include fluorescent dyes, chemiluminescent compounds, radioisotopes, electron-dense reagents, enzymes, colored particles, biotin, or dioxigenin. The label component can generate a measurable signal, such as radioactivity, fluorescent light, color, or enzyme activity, which can be used to identify and quantify the amount of label bound to a test site. Thus, the label component can also represent the presence of a particular antigen bound thereto.

In certain embodiments, the label component preferably comprises a gold colloid having a mean particle size of about 50 nm to about 100 nm prior to formation of the labeled conjugate More preferably, the mean particle size can range from about 60 nm to about 80 nm prior to formation of the labeled conjugate. Such label components particularly are described in U.S. Patent Publication No. 2008/0213920, which is incorporated herein by reference in its entirety.

In embodiments wherein the device of the invention makes use of a sandwich technique, the antibody used in the detection comprises a binding region or site which binds to an epitope on the analyte for detection, such as FSH. The antibody preferably has a label component bound thereto to form a conjugate, which reacts with the analyte for detection to form a complex in the liquid sample. The analyte bound with the conjugate reacts with a capture antibody to form a "sandwich" of the capture antibody, analyte, and conjugated antibody. In certain embodiments, a biotinylated capturable antibody can also be utilized. For example, the biotinylated capturable antibody can include a region or site that binds to a second epitope of the analyte. In these embodiments, the resulting "sandwich" comprises a complex of the labeling antibody (i.e., labeled conjugate)—analyte—biotinylated capturable component. In general, the sandwich complex is progressively produced as the test liquid with the analyte therein continuously moves along the test strip of the device. As more and more conjugate is immobilized, the label components aggregate and become visible through a viewing window, indicating the presence of a particular analyte in the liquid sample.

Embodiments of the invention can include one or more standards or internal controls that allow for determination of whether signal development (e.g., color development) is a true indication of the presence or absence of analyte (e.g., FSH) in the sample or is simply an artifact, such as caused by nonspecific sorption. For example, in one embodiment employing the sandwich technique, the standard consists of a negative control site, preferably disposed adjacent the test site, and visible through a second window proximate the first. The negative control site preferably is prepared identically to the test site, except immobilization of the binding protein is omitted. Therefore, although the conjugate will reach the site, it aggregates due only to non-specific binding. If the test site is not appreciably more intense in color than the control site, the assay is considered negative.

In certain embodiments, the device can include a positive control. Thus, when exploiting the sandwich technique for example, a cell may have an authentic sample of the analyte for detection immobilized at a control site. If no color develops at this control site, the assay is considered inconclusive.

In yet another embodiment, which can be particularly useful when the fertility test device comprises a biphasic test strip medium, the biphasic medium comprises a control site disposed on the capture medium downstream of the test site. The control site has immobilized thereon at least one capture protein. The primary function of the control site is to capture and immobilize the label antibody which has not been captured at the test site.

According to various embodiments, the control site can include polyclonal antisera specific for the label antibody. Indication of the presence of the label component at the control site indicates proper functioning of the test, irrespective of the presence or absence of analyte in the sample. Preferably, both the capture and control sites are visible through the window of the casing. In a preferred embodiment, the device incorporates a biphasic chromatographic medium (or test strip) which enhances the speed and sensitivity of the assay. Generally, a biphasic substrate element useful according to the invention comprises a release medium joined to a capture medium located downstream of the release medium. The release and capture media preferably comprise two different materials or phases having different specific characteristics. The two phases are joined together to form a single liquid path such that a solvent front can travel unimpeded from the proximal (upstream) end of the release medium (which can be defined as a first portion of the device) to the distal (downstream) end of the capture medium (which can be defined as a second portion of the device).

Reagents for detecting, labeling, and capturing an analyte of interest are disposed on the release and capture media. In certain embodiments, a labeled conjugate is located on the release medium and includes a binding member reactive with a particular site (sometimes referred to as a "first epitope") on the analyte of interest. The labeled conjugate further comprises a detectable marker (or label), preferably colloidal gold. A capturable conjugate can be located on the release medium downstream of the binding member, which conjugate comprises an antibody with a binding region reactive with another particular site (sometimes referred to as a "second epitope") on the analyte of interest. The first epitope and the second epitope are preferably different sites on the analyte. The capturable conjugate also comprises one member of an affinity pair and is capable of forming a sandwich complex with the labeled binding member and the analyte. The labeled conjugate and the capturable conjugate both are releasably bound to the release medium such that when the solvent front created by the liquid sample being analyzed passes through the release medium, the labeled conjugate and the capturable conjugate both become mobilized by the liquid and flow with the solvent along the liquid path. In operation, if any analyte is present in the liquid sample, it preferably reacts first with the labeled conjugate, then with the capturable conjugate as the front advances along the liquid path to form a diffusible sandwich which is then transported by capillary action. Thus, by the time the solvent front reaches the capture medium section of the biphasic material, the capturable sandwich complex has formed.

In embodiments such as those described above, the capture medium contains the reagent used to capture the complex described above. Generally, the reagent is located on a test site and comprise the other member of the affinity pair specific for the capturable affinity moiety. Upon diffusion into the capture medium, the diffusible sandwich becomes concentrated by the interaction of the capture affinity member with the capturable affinity moiety yielding a visual signal. The affinity member is immobilized, preferably by simple adsorption, at the test site, and does not advance with the liquid front.

The release medium can be formed from a material which allows for release of indicator reagents. In certain embodiments, the release medium comprises a bibulous, hydrophilic material, such as absorbent materials. Preferred materials for use as a release medium include, but are not limited to, cotton linter, cellulosic materials, or materials made of cellulose together with a polymeric fibrous material, such as polyamide or rayon fibers, and glass fiber material. The primary function of the release medium is first to support and to subsequently release and transport various immunological components of the assay, such as a labeled conjugate and/or a capturable conjugate, both of which can bind the analyte of interest. This release and transport occurs during routine operation of the assay. Generally, the release medium can be formed of any material capable of performing the function of holding, releasing, and transporting various immunological parts of the test such as the labeled test component.

Specific, non-limiting examples of materials useful in forming the release medium include: cotton linter paper, such as S&S 903, S&S GB002, and BFC 180 (available from Whatman, Fairfield, N.J.); cellulosic materials, such as Grade 939 made of cellulose with polyamide, Grade 989 made of cellulose blend fiber, and Grade 1278 and Grade 1281 made of cellulose and rayon with polyamide (available from Ahlstrom Corporation, Mt. Holly Springs, Pa.); and glass fiber, such as Lydall borosilicate (available from Lydall, Inc., Rochester, N.H.). The release medium preferably is coated with an aqueous solution containing bovine serum albumin (BSA) and a nonionic surfactant, such as Triton X-100 (available from Rohm & Haas Co., Philadelphia, Pa.) in order to prevent nonspecific binding and facilitate release of the diffusible reagents. A combination of about 3% BSA and about 0.1% Triton X-100 is useful for this purpose.

The capture medium can be formed from a material which permits immobilization of reagents for detection of the presence of analyte in the test fluid. The capture medium generally comprises hydrophilic polymeric materials, such as microporous films or membranes, which permit protein reagents to be immobilized directly on the membrane by passive adsorption without the need for chemical or physical fixation. Of course, the use of chemical or physical fixation is not precluded by the invention, and any known method for immobilizing the reagents to the membrane can be used.

Non-limiting examples of materials useful as the capture medium comprise a microporous polymeric film of nitrocellulose, nylon (e.g., nylon 66), or similar materials, or combinations of such materials. Materials for use as the capture medium preferably have a pore size in the range of from about 5 µm to about 20 µm. In specific embodiments, the nitrocellulose membrane may be nitrocellulose alone or a mixed ester of nitrocellulose, such as in combination with an ester of nitric acid and/or other acids. The nitrocellulose membrane preferably is coated or laminated onto a translucent or transparent polymeric film to provide physical support for the membrane.

In a preferred embodiment, a nitrocellulose polymer which has been cast onto a polyester film, such as MYLAR®, is used. Alternatively, a nitrocellulose membrane laminated onto a polyester film also may be used, although other backing materials besides polyester may be used. Pre-laminated or pre-cast sheets useful in the present invention are commercially available, for example, from Millipore Corporation, Bedford, Mass. and Sartorius Corporation, Edgewood, N.Y. Both media are in the form of planar strips, which are joined together to form a single flow path.

In one embodiment, the release medium and capture medium are joined by overlapping the downstream edge of the release medium over the upstream edge of the capture medium, then adhering the resulting biphasic material to a clear polymer film or sheet, thereby holding the media in place. The overlapping region allows for the efficient and rapid transfer of analyte containing fluid from the release medium to the capture medium.

While the rapid transfer associated with the overlapping region is useful, the manufacturing issues associated with reproducibly generating a small overlapping region, such as necessary with small devices, can be difficult. Therefore, in certain embodiments, the invention also provides a test device having a biphasic design as described herein but wherein the release medium and the capture medium do not overlap but rather are connected by a non-overlapping butt joint. In such embodiments, the fluid front moving along the test strip is transferred from the release medium to the capture medium through bridging the non-overlapping region by capillary action.

The butt joining of the phases can maintain the same efficacy of the overlapping of the phases, even after accelerated aging of the devices. Thus, the use of a butt joint simplifies the manufacture of the present test device without any loss of performance in the device.

The diffusible and non-diffusible reagents can be applied to the release and capture media, respectively, by any suitable technique. In one embodiment, the diffusible antibody reagents are applied to the release medium by direct application onto the surface of the medium and dried to form a narrow band. The non-diffusible reagents preferably are applied to the capture medium by passive adsorption.

In one preferred embodiment, the device comprises a casing defining a sample inlet, a test volume, and reservoir volume. Disposed within the casing are a sample absorbent, the biphasic chromatographic substrate(s), and reservoir absorbent. The sample absorbent is preferentially disposed within the casing and extending to the exterior thereof. Located downstream of the sample absorbent is the biphasic chromatographic substrate comprising a release medium and a capture medium joined together to form a single liquid path. The release and capture media can be laminated onto a transparent plastic film or sheet.

The sample absorbent preferably is a bibulous hydrophilic material which facilitates absorption and transport of a fluid sample to the biphasic chromatographic medium. Such materials may include cellulose acetate, hydrophilic polyester, and other materials having similar properties. Further, a combination of absorbent materials also may be used. Non-limiting examples of useful materials include bonded cellulose acetate, bonded polyolefin, or hydrophilic polyester, such as those materials commercially available from Filtrona Fibertec Company (Colonial Heights, Va.). Other useful materials include absorbent matrices, such as Grade 939, Grade 989, Grade 1278, or Grade 1281, available from Ahlstrom Corporation. The sample absorbent preferably is coated with a buffered solution containing BSA and a nonionic surfactant, such as Triton X-100. The presence of BSA and surfactant minimize non-specific adsorption of the analyte. A concentration of about 1% BSA and about 0.2% surfactant in tris buffer can be effective for this purpose.

By providing a reservoir of sorbent material disposed beyond the chromatographic substrate, a relatively large volume of the test liquid and any analyte it contains can be drawn through the test area to aid in background clearance and enhance sensitivity. The reservoir material preferably comprises a hydrophilic material which may be the same as the upstream sample absorbent. The reservoir absorbent generally facilitates capillary action along the chromatographic substrate and absorbs excess liquid contained within the device. The reservoir absorbent preferably compromises absorbent paper made from cotton linter fibers, such as CF3, CF4, CF5 or 470 (available from Whatman) or cellulosic materials, such as Grade 3MM (available from Whatman) and Grade 320 (available from Alhstrom).

In using a device according to various embodiments of the invention, the liquid sample being analyzed is preferably applied to a sample absorbent which is in contact with the proximal end of the biphasic substrate. The casing of the device may be configured to permit direct contact with a body fluid or as a dipstick for dipping in a container of body fluid or other test solution. The liquid sample travels impelled by surface effects such as by capillary action along the liquid path formed by the substrate. More specifically, the test sample passes through the biphasic chromatographic substrate and into reactive contact with the test site (and optionally one or more control sites). Preferably, at least the test site is visible to a user, such as through one or more windows in the device's exterior casing. In a preferred embodiment, the labeled binding member recognizing the analyte is disposed in preserved form on the release medium in the flow path within the device.

In one embodiment, if the analyte of interest is present in the sample, it passes through the inlet and the interior of the device where it sequentially reacts with the labeled antibody and the capturable antibody with the affinity agent, thereby forming the capturable sandwich complex. The complex formed by the analyte, labeled antibody, and the capturable antibody then reacts with the immobilized capture component at the test site, the capture component being specific for the affinity agent on the capturable antibody. This process results in the labeled complex accumulating at the test site.

The presence of the analyte is determined by observing the presence of the detectable marker at the test site. If no analyte is present in the sample, the capturable complex does not form and no detectable marker will be present at the test site. If a reference site is present, the unbound complex or the free labeled binding member can accumulate at the reference site.

In another embodiment, the device for detecting FSH in a liquid sample includes a release medium having a labeled conjugate comprising a detectable label and a first binding member reactive with a first epitope of FSH. The device also includes a capture medium in fluid communication with the release medium. The capture medium includes a test site having immobilized thereon a capture component capable of directly or indirectly binding FSH and a reference site having immobilized thereon a capture component comprising a binding member reactive with the labeled conjugate. In such embodiments, the color intensity of the reference site is calibrated such that when a predetermined level of FSH is present within the sample the color intensity of the reference site will match that of the test site. Preferably, the predetermined level correlates to an amount of FSH that would be deemed to be elevated. Accordingly, the assessment of FSH in the sample is based on a comparison of resulting color intensities at the test site and reference site. When the color intensity of at the reference site is equal to or darker than the color intensity at the test site, the FSH level in the sample is deemed to be at or above the predetermined level.

In one embodiment, the device includes a sample application member for receiving the liquid sample. The sample application member is in fluid communication with a first portion (e.g., release medium). The first portion includes a labeled conjugate with a detectable label and a first binding member reactive with a first epitope of FSH. The labeled conjugate is present in excess relative to an amount of labeled conjugate necessary to bind the FSH present at a predetermined level. The first portion is in fluid communication with a second portion (e.g., a capture medium). The second portion includes a test site having immobilized thereon a capture component capable of directly or indirectly binding FSH bound to the labeled conjugate and a reference site having immobilized thereon a capture component including a binding member that binds a portion of the excess amount of the labeled conjugate. Preferably, the device includes a reservoir for containing liquid sample and excess labeled conjugate not captured at the test site and the reference site. In such an embodiment, the color intensity of the reference site is calibrated to be inversely proportional to the concentration of FSH present in the sample. Preferably, the color intensity of the reference site is calibrated such that when the FSH is present in the sample at the predetermined level, the color intensity of the reference site matches the color intensity of the test site. As such, the assessment of the FSH level in the sample is based on the comparison of resulting color intensities at the test site and reference site.

In preferred embodiments, the labeled antibody striped on the device is present in excess relative to the amount of labeled antibody required to bind the predetermined level of FSH. More preferably, the labeled antibody is present in an amount greater than twice the amount required for binding the predetermined level of FSH. Thus, when FSH levels are present within the sample at the predetermined level, a portion of the labeled antibody which is significantly less than the total labeled antibody (e.g., less than half) will bind to FSH and be available for capture at the test site. To compensate for the excess label antibody present within the system, the color intensity of the reference site is calibrated so that the color intensity of the reference site will match the color intensity of the test site when a sample includes the predetermined level of FSH. The calibration of the reference site can be carried out by titrating the reference site with varying antibody amounts so that the color intensity of the reference site matches the color intensity of the capture site when the predetermined level of FSH is present. In such embodiments, only a portion of the excess labeled antibody that passes the test site will be retained at the reference site. The excess labeled antibody not bound at either the test site or the reference site will then flow past both sites and into the reservoir material. In certain embodiments, the test site includes a capture component comprising a second binding member that is reactive with a second epitope of FSH, such that in the presence of FSH in the sample, a sandwich complex is formed at the test site comprising the labeled conjugate, FSH, and the capture component. In another embodiment, the release medium includes a biotinylated capturable component comprising a second binding member reactive with a different epitope of FSH, such that in the presence of FSH in the sample, a complex is formed comprising the labeled conjugate, FSH, and the biotinylated capturable component. In such embodiments, the capture component comprises streptavidin, polymerized streptavidin, neutravidin, or combination thereof.

In yet another embodiment, the device for detecting FSH present in a liquid sample at a concentration relative to a predetermined level includes a sample application member for receiving the liquid sample. The sample application member is in fluid communication with a first portion (e.g., release medium). The first portion includes a labeled conjugate with a detectable label and a first binding member reactive with a first epitope of FSH. The first portion is in fluid communication with a second portion (e.g., capture medium). The second portion includes a single test site having immobilized thereon a capture component capable of directly or indirectly binding FSH. The device is calibrated such that a signal indicating binding of FSH at the test site only occurs when FSH is present in the liquid sample at a concentration above the predetermined level. No signal (e.g., color development) at the test site indicates any FSH in the liquid sample is present at a concentration below the predetermined level. In this way, the assessment of FSH level is based on the color development or lack thereof at one site, namely the test site. In such embodiments, the calibration comprises the use of a scavenger component located between the sample application member or sample deposit site and the test site. The scavenger component binds any FSH present in the sample below the predetermined level.

In yet another embodiment, if the analyte of interest is present in the sample, it passes through the inlet and the interior of the device where it reacts with a labeled antibody which is releasably attached to the release medium. The liquid sample wicks across the release medium and forms a complex with a capture antibody which is immobilized on the capture medium and defining a test site. As the sample front passes across the test site, a sandwich complex is formed comprising the analyte, labeled antibody, and the capture antibody. Preferably, such embodiments include a scavenger component comprising either an antibody having a binding member that reacts with the analyte (e.g., FSH) or an antibody or protein (such as streptavidin) that reacts with a member of the sandwich complex. The amount of the scavenging component striped onto the test device can be calibrated to bind with an amount of the analyte equal to a predetermined level. Samples containing an excess level of the analyte consume all of the scavenging component while the remaining analyte binds to the labeled conjugate and ultimately results in the formation of a labeled complex accumulating at the test site.

The presence of the analyte (e.g., FSH) is determined by observing the presence of the detectable marker at the test site. If no analyte is present in the sample, the complex does not form and no detectable marker will be present at the test site. In this way, the results of this embodiment are similar in nature to a pregnancy test kit. If a control site is present, the excess labeled binding member will accumulate at the control site.

Illustrations of one embodiment of a test device 5 according to the present invention are shown in FIGS. 1A-E. The test device 5 comprises an outer, molded casing 10 which defines a hollow, elongate enclosure. The casing 10 includes a test liquid inlet 14 and an opening 16 comprising a window through which the test site (reference site and control site, if applicable) is visible. As illustrated in FIGS. 1A-E, the window 16 is disposed on a side of the casing 10 opposite the sample inlet 14. This configuration reduces the incidence of contamination of the test site which is disposed in the interior of casing 10 and is exposed through the window 16. The casing 10 further defines vent openings 38, 40, and 42 located along the sides and at the distal end of the casing 10. The vent opening 38 reduces the incidence of "vapor lock" within the device during use. The presence of the openings 40 and 42 help to reduce "flooding" of the chromatographic substrate, which may occur when the user applies too much sample to the device.

A preferred embodiment of the test device 5 is illustrated in FIGS. 2A-E. As seen therein, the test device 5 comprises an outer, molded casing 10 which defines a hollow, elongate enclosure. The casing 10 includes an opening 16 comprising a window through which the test site (and control site, if applicable) is visible. The test device 5 further includes a test liquid inlet 14, which is covered by a removable cap 60. In this embodiment, the test liquid inlet 14 is external to the casing 10 and is covered by the cap 60 except when in use. Providing the test liquid inlet 14 external to the casing 10 allows for ease of application of the test liquid to the test device 5, such as by placing the test liquid inlet 14 in the path of a urine stream or dipping in a container holding the test liquid. The cap 60 is re-attachable (such as "snap-fitting" onto the lip 62 extending from the casing 10) and can be replaced after application of the test liquid to avoid contamination of the sample while the test is proceeding. The test liquid inlet 14 external to the casing can be a portion of the absorbent material 12, as illustrated in FIG. 3 and described below. In further embodiments, the test liquid inlet 14 can be a portion of the biphasic chromatographic substrate 18. The casing 10 further includes a test strip support 70 located on the bottom surface of the casing 10.

A specific embodiment of the assay materials for use according to the invention is illustrated in FIG. 3. When the device is fully assembled, the assay materials of FIG. 3 preferably are disposed inside a casing. The assay materials comprise an absorbent material 12, a biphasic chromatographic substrate 18, and a reservoir material 24. The assay materials and the interior of the casing together define a flow path. When the inlet 14 is disposed within or otherwise in contact with a liquid sample, the liquid is transported by capillary action, wicking, or simple wetting along the flow path downstream through the absorbent 12, along the chromatographic substrate 18, and into the reservoir 24, generally as depicted by the arrow. The absorbent material also serves as a filter which can remove from impure test samples particulate matter and interfering factors.

Illustrated in FIG. 4 is a biphasic chromatographic substrate 18, comprising a release medium 30 and a capture medium 32. The horizontal dashed line represents the interface between the release medium 30 and the capture medium 32. As previously noted, this interface can be in the form of an overlapping relationship. Alternatively, the release medium 30 can be butted up to the capture medium 32. Releasably disposed on the release medium 30 is a band 26 of labeled binding member, e.g., an antibody-metal sol. In one embodiment, the labeled biding member is in dehydrated form. As the liquid sample moves past the band 26, the labeled binding member becomes entrained in the liquid, reconstituted (in the case of a dehydrated binding member), and reacts with any analyte present in the liquid sample. Disposed downstream of the labeled binding member is a band 28 of preferably dehydrated capturable conjugate. The capturable conjugate comprises a binding member which binds to a second epitope of the analyte, e.g. an antibody, and a capturable affinity component, e.g. biotin. The capturable conjugate also becomes entrained in the liquid sample as it advances along the substrate 18.

Immobilized on the capture medium 32 are, respectively, the test site 34 and the reference site 36. In FIG. 4, the reference and test sites are illustrated as being disposed serially along the flow path. Alternatively, the reference and test site or sites may be disposed side by side or in other spatial relationships. The test site 34 comprises a pre-selected quantity of a capture affinity member specific for the capturable affinity component disposed on the release medium. For example, when the capturable affinity member is biotin, the capture component may be streptavidin. Of course, any such complementary system of components could be used in place of biotin and streptavidin. The reference site 36 typically comprises immobilized antisera, antibody, or other protein specific for the labeled binding member and is thus also capable of binding the labeled binding member.

In certain embodiments, as illustrated in FIG. 5, a band 26 of labeled binding member, e.g., an antibody-metal sol, and a band 28 of capturable component e.g., antibody-biotin, can be releasably disposed on the release medium 30. In one embodiment, both the labeled binding member and the capturable component are in dehydrated form. As the liquid sample moves past the bands 26 and 28, the labeled binding member and capturable components becomes entrained in the liquid, reconstituted (in the case of a dehydrated binding member and capturable component), and reacts or binds with a particular analyte or analytes of interest present in the liquid sample. Accordingly, the resulting conjugate comprising a binding antibody, a label component, an analyte for identification (e.g., FSH), and the capturable component advances along with the sample front until the reaching the test site 34. In this particular embodiment, the test site includes at least one immobilized capture component having a binding member which binds to the capturable component. Accordingly, a "sandwich" including the desired analyte is maintained at the test site 34. If desired, a reference site 36 can include an antibody or a protein specific for the labeled binding member and is thus also capable of binding the labeled binding member. In this regard, the reference site also acts as a control site.

A side view of one embodiment of the operative portion of the assay materials is schematically illustrated in FIG. 6. As shown, the absorbent material 12 is disposed proximate the release medium 30, and overlaps the release medium 30 at one end. The release medium 30 in turn overlaps the capture medium 32, which is disposed distal to the release medium 30. Again, the release medium 30 and the capture medium 32 may alternatively be connected via a butt joint rather than being in overlapping connection. The reservoir 24 overlaps the distal end of the capture medium 32. These four components together form a single fluid path, and they cooperate to cause sample liquid to flow from the absorbent 12 along the release medium 30 and the capture medium 32 into the reservoir 24.

The invention is not limited by the precise nature of the test site 34 and the corresponding reference site 36. Antibody or other affinity agent can be immobilized at the test site 34 and the reference site 36 using absorption, adsorption, or ionic or covalent coupling, in accordance with methods known per se. The capture medium 32 preferably is selected to bind the capture reagents without the need for chemical coupling. Nitrocellulose and nylon both permit non-chemical binding of the capture component and reference reagent.

Disposed downstream of the capture medium 32 is the reservoir 24 comprising a relatively large mass of absorbent or superabsorbent material. The purpose of reservoir 24 is generally to ensure that a reasonably large amount of test liquid is drawn across the chromatographic medium. In certain embodiments, the sample absorbent 12 can be omitted, and the release medium 30 can itself act as the sample absorbent. Such embodiments of the assay materials are useful in performing dipstick assays.

Detection Using an Avidin-Biotin Format

In one aspect, the present invention provides devices wherein detection includes direct binding and detection of FSH. In various embodiments, the release medium includes a labeled conjugate (e.g., gold colloid labeled anti-FSH antibody) comprising the detectable label and a first binding member that is reactive with a first epitope of FSH. The release medium also includes a biotinylated capturable component (e.g., biotinylated anti-FSH antibody) comprising a second binding member that is reactive with a second epitope of FSH. Each of the labeled conjugate and the biotinylated capturable component are striped on the release medium. The capture medium of the test device includes a test site having a capture component. Preferably, the capture component comprises neutravidin, streptavidin or its polymer. The advantages of polymeric streptavidin are described in U.S. Patent Publication No. 2008/0213920, which is incorporated herein by reference. The capture medium can also include a reference site and/or a control site. Each of these sites includes an antibody or an IgG binding protein (e.g., Protein A or Protein G) immobilized on the capture medium (e.g., nitrocellulose section). In some embodiments, the reference site also acts as the control site.

In preferred embodiments, the reference site serves as an "active" or "non-fixed" reference site, whereby the color intensity of the reference site changes with the amount of FSH present within the sample. In certain embodiments, the color intensity at the reference site is calibrated to the approximate color intensity of the test site when the amount of FSH is considered at the elevated level. The test results are conveyed to the consumer using a color matching method, namely comparing the color intensities of the test site and reference site. If the color intensity at the test site is lighter than that of the reference site, the FSH level of the subject is deemed normal. To the contrary, if color intensity at the test site is equal to or darker than that of the reference site the FSH of the subject is deemed elevated.

As referenced above, the color intensity of the reference site is preferably calibrated to correlate with the color intensity at the test site for a predetermined concentration or amount of FSH. For example, a predetermined level of FSH (e.g., lowest concentration deemed as being elevated) can be selected and an amount of labeled conjugate can be selectively applied to the release medium so that if a sample contains the predetermined level of FSH then a portion of the labeled conjugate will bind the FSH and be captured at the test site while the remainder of the labeled conjugate will pass the test site and a portion shall bind at the calibrated reference site, with any excess labeled conjugate flowing past the reference site. In such a case, color intensity at the test site and the reference site should be practically equal and signal that the sample contained the predetermined level of FSH. In the event that the sample has an FSH concentration above the predetermined level, the color intensity of the reference site will be lighter than the color intensity of the test site. Thus, indicating that the FSH concentration of the sample was elevated. If the color intensity of the reference site is darker than that of the test site, then the FSH concentration of the sample was normal.

In such embodiments, the active reference site has a color intensity that is inversely proportional to the levels of FSH present within the sample. As FSH levels increase, more labeled "sandwiches" comprising the labeled conjugate-FSH-biotinylated antibody are formed and captured at the test site through an avidin-biotin interaction. As a result, less labeled conjugate (e.g., gold colloid labeled anti-FSH antibody) is available to flow past the test site to be bound at the reference site. Thus with higher levels of FSH, there are lower levels of gold labeled antibody (for example only) bound at the reference site, resulting in a lower color intensity at the reference line. This is illustrated below in Table 1.

TABLE 1

Changes of the Reference Line Color Intensity (Optical Density) with FSH Standards

| FSH Standard (mIU/mL) | Average Reference Line Intensity (OD) |
|---|---|
| 4 | 12.4 |
| 8 | 12.0 |
| 12 | 11.5 |
| 16 | 10.9 |

The release medium, according to one embodiment of the present invention, includes a labeled conjugate comprising the detectable label and a first binding member reactive with a first epitope of FSH and a biotinylated capturable component including a second binding member reactive with a second epitope of FSH. As such, when a sample includes FSH, a complex is formed comprising the labeled conjugate, FSH, and the biotinylated capturable component. In such embodiments, the capture medium comprises a test site having immobilized thereon a capture component comprising streptavidin, polymerized streptavidin, neutravidin, or combination thereof.

According to embodiments including streptavidin as a capture component, the streptavidin used in the preparation of test devices according to the invention preferably comprise a streptavidin solution that can be applied to the test device, thereby immobilizing streptavidin on the substrate. The streptavidin in the solution can comprise a number of polymerized forms, such as dimeric, trimeric, tetrameric, or the like. While monomeric streptavidin can be present in the solution, the solution preferably comprises a majority of polymerized streptavidin, the total content of any monomeric streptavidin in the solution comprising only a minority of the total content of the solution. Specifically, the streptavidin solution can comprise polymerized streptavidin in an amount such that the polymerized streptavidin comprises at least 50% by weight of the streptavidin solution. Preferably, the solution comprises at least about 55% by weight, at least about 60% by weight, at least about 75% by weight, or at least about 90% by weight of polymerized streptavidin.

In one preferred embodiment, the test device, wherein the device includes a release medium formed of a first material and comprising a labeled conjugate comprising a detectable label and a first binding member reactive with a first epitope of FSH and a biotinylated capturable component comprising a second binding member reactive with a second epitope of FSH, such that in the presence of FSH in the sample, a complex is formed comprising the labeled conjugate, FSH, and the biotinylated capturable component. The device also includes a capture medium in fluid communication with the release medium and formed of a second, different material. The capture medium includes a test site having immobilized thereon a capture component comprising streptavidin, polymerized streptavidin, neutravidin, or combination thereof. Preferably, the capture medium also includes a reference site separate from the test site. The reference site has immobilized thereon a capture component comprising a binding member reactive with the labeled conjugate. As described above, the reference site is preferably "active" in the sense that the resulting color intensity of the reference site changes based on the amount of FSH present in the sample.

FIGS. 7A-7D and 8A-8D each illustrate results obtained according to embodiments of the present invention. Since each Figure illustrates a result used to assess the FSH level in the liquid sample based on the comparison of resulting color intensities at the test site 34 and reference site 36, the respective color intensity of each site is assigned a numeric value ranging from 1 to 4 with the numeric value of 4 representing the darkest or most prominent color intensity and the numeric value of 1 representing no visible color development. Although only four different color intensities are illustrated in the Figures, a full spectrum of resulting color intensities is available according to embodiments of the present invention. That is, FIGS. 7A-7D and 8A-8D along with the numeric characterization of the respective sites is meant to be illustrative of embodiments of the present invention and should not be construed as limiting in any way.

FIGS. 7A-7D each illustrates a different result obtained according to one embodiment of the present invention. As shown in FIG. 7A, the results of a fertility test are viewed through a window 16 (represented by dotted lines). In FIG. 7A, the test site 34 exhibits no color development (e.g., a color intensity of 1) while reference site 36 exhibits a strong dark color (e.g., a color intensity of 3). As referenced above, when the color intensity of the reference site 36 is darker than that of the test site 34 (e.g., 3>1) then the FSH concentration of the sample is normal. As such, FIG. 7A illustrates a test result depicting a normal level of FSH. Similarly, FIG. 7B also depicts a test result for a sample having normal FSH. As shown in FIG. 7B, the test site 34 exhibits a slight to moderate color intensity (e.g., a color intensity of 2) while the reference site 36 exhibits a significantly darker color development (e.g., a color intensity of 3). By comparing the color intensities of the test site 34 and the reference site 36, a user can readily determine that the color intensity at the test site is less than that of the reference site (e.g., 2<3). Thus, the results shown in FIG. 7B depict a normal level of FSH in the sample.

FIGS. 7C-7D each depict test results in which the sample included an elevated level of FSH. In particular, FIG. 7C shows test results in which the test site 34 and the reference site 36 each exhibit a similar or slight to moderate color intensity (e.g., color intensity of the test site and the reference site are both 2). As described above, the color intensity of the reference site 36 is preferably calibrated to correlate with the color intensity at the test site 34. For example, a predetermined level of FSH (e.g., lowest concentration deemed as being elevated) can be selected and an amount of labeled conjugate can be applied to the release medium so that if a sample contains the predetermined level of FSH then roughly half of the labeled conjugate will bind the FSH and be captured at the test site while the other half of the labeled conjugate will pass the test site and bind at the reference site. In such a case, color intensity at the test site and the reference site should be practically equal and signal that the sample contained the predetermined level of FSH. Accordingly, the equal color intensities convey to the user that the sample contained the predetermined level of FSH. The test results exemplified in FIG. 7D illustrate a level of FSH significantly greater than the predetermined level. For instance, the color intensity of the test site 34 is significantly darker (e.g., a color intensity of 3) than that of the reference site 36 (e.g., a color intensity of 2).

In another embodiment, the capture medium also includes a control site positioned separate from the reference site and the test site. In such embodiments, the release medium can include a labeled control conjugate comprising a detectable label and an antibody that is not reactive with FSH. The control site has immobilized thereon a capture component having a binding member reactive with the labeled control conjugate. Accordingly, the labeled control conjugate will travel along the solvent front of the liquid sample and ultimately bind with the capture component immobilized at the control site. Preferably, the control site is located downstream of both the test site and the reference site. As such, the detection of the labeled conjugate at the control site informs a user that the liquid sample has in fact traveled the downstream and past both the test site and the reference site.

In embodiments having a separate or independent control site and reference site, the release medium includes a labeled control conjugate comprising a detectable label and an antibody that is not reactive with FSH. In such embodiments, the control site has immobilized thereon a capture component having a binding member reactive with the labeled control conjugate. For instance, the labeled control conjugate can comprise an antibody derived from a species different than the label conjugate for binding FSH. The labeled control conjugate can be added to the release medium with and at the same location as the labeled conjugate for binding FSH. By way of example only, the labeled conjugate for binding FSH can be mouse derived and the labeled control conjugate can be sheep derived. Preferably, the reference site is calibrated to the approximate color of the test site when the predetermined level of FSH is present in the liquid sample being tested. Furthermore, the antibody or capture component immobilized at the control site specifically recognizes the antibody of the labeled control conjugate. For instance, if the antibody on the labeled control conjugate is derived from sheep, the capture component at the control site would be anti-sheep IgG antibody. The control line in this format can be positioned either upstream or downstream of the reference line but downstream from the test site.

FIGS. 8A-8D each illustrates a different result obtained according to one such embodiment of the present invention. As shown in FIG. 8A, the results of a fertility test are viewed through windows 16 and 17 (represented by dotted lines). Window 16 allows a user to view the test site 34 and the "active" reference site 36 in close proximity to each other, while window 17 allows a user to view the control site 38. In FIG. 8A, the test site 34 exhibits no color development (e.g., a color intensity of 1) while reference site 36 and the control site each exhibit a strong dark color (e.g., a color intensity of 3). As referenced above, when the color intensity of the reference site 36 is darker than that of the test site 34 (e.g., 3>1), the sample contained a normal concentration of FSH. The color development at the control site confirms that the liquid sample and the releasable reagents were effectively conveyed throughout the test device. FIG. 8B also depicts test results for a sample containing a normal level of FSH. In particular, the slight color intensity of the test site (e.g., a color intensity of 2) is clearly less than that of the reference site 36 (e.g., a color intensity of 3). Thus, these sample results depict a normal level of FSH.

FIGS. 8C-8D each illustrate test results in which the sample contained an elevated level of FSH (e.g., the specified predetermined level or greater). FIG. 8C depicts results in which the color intensity of the test site 34 (e.g., a color intensity of 3) and the reference site 36 (e.g., a color intensity of 3) are the same or substantially similar. As such, the sample contained a concentration of FSH at or above the predetermined level of FSH. As shown in FIG. 8C, the control site 38 (e.g., a color intensity of 3) in these results exhibits a dark color intensity signaling that the liquid sample and the releasable reagents traveled throughout the test device. As shown if FIG. 8D, the test site 34 (e.g., a color intensity of 4) exhibits a color intensity greater than that of the reference site 36 (e.g., a color intensity of 3). Such visual test results convey to the user that the sample contained an elevated level of FSH (e.g., the test site color intensity of 4 is greater than the reference site color intensity of 3).

Accordingly, such embodiments of the present invention provide a quick, non-intrusive, and convenient means for determining a user's ovarian reserve by simply comparing the resulting color intensities of the test site and the reference sites. Furthermore, a user can also establish that the particular test device is functioning by simply viewing a resulting color development at the control site.

Detection Using A Scavenging Component

While the detection of FSH in either the traditional or avidin-biotin lateral flow assay allows the direct or indirect capture of FSH, or FSH complex, alternative methods can be employed to determine the presence of FSH above a predetermined level through the use of a monoclonal or polyclonal scavenger antibody or a combination of avidin and polymerized streptavidin. Such embodiments generally include scavenger site or line, either in solution or immobilized, that is capable of capturing either FSH, or a labeled antibody-FSH complex, or a labeled antibody-FSH-biotinylated antibody sandwich. In practical terms, this serves to 'subtract' the predetermined levels of FSH present within the sample prior to reaching the test site, effectively removing that FSH from the sample as it flows down the test strip. One advantage of the scavenger format is that it allows a preset amount of FSH to be subtracted from the sample (i.e., levels of FSH equal to the predetermined level) therefore only allowing FSH levels above the predetermined level to be captured at the test site. Determination of the FSH levels in the scavenger assay format is different from that used in the color matching FSH assay formats. Since the predetermined level of the assay is controlled by the scavenger line design, test result interpretation will be similar to the current pregnancy tests in which the detection of the labeled conjugate at the test site indicates elevated FSH levels. For example, when FSH is present in levels equal to or above the predetermined cutoff level, the color developed at the test site informs the user that their FSH level is elevated. On the other hand, when no discernible color is present at the test site, the FSH level would be deemed normal. In this way, the results obtained while using a scavenger component are similar in nature to pregnancy test kit.

The present invention provides devices wherein the detection is facilitated through selective removal or subtraction of a predetermined amount of FSH. Such embodiments can particularly include a scavenger component that is reactive with FSH. In certain embodiments, the scavenger component comprises an antibody that is selectively reactive with FSH. In various embodiments, the scavenger component can be located at any position between the location of sample deposit and the test site. In accordance with such embodiments, at least one of the release medium and the capture medium includes a binding member that is reactive with FSH to bind and ultimately capture any FSH present in the sample exceeding the predetermined level of FSH scavenged by the scavenging component.

In one embodiment, the device includes a release medium comprising a labeled conjugate including a detectable label and a first binding member that is reactive with a first epitope of FSH while the capture medium comprises a test site including a second binding member that is reactive with a second epitope of FSH. In one embodiment, the scavenger antibody can be releasably attached to the biphasic substrate from any location between a sample deposit location and the test site. As such, if FSH is present in the sample, a complex is formed comprising the labeled conjugate, FSH, and the scavenger component. Once the predetermined level of FSH has been reached, a complex is formed comprising the labeled conjugate, FSH, and the immobilized binding member. In one preferred embodiment, the scavenger component can be located downstream from the sample deposit and up to and including a region including the labeled conjugate. In another embodiment, the scavenger component can be located between a region including the labeled conjugate and a region including the test site. In yet another embodiment, the scavenger component can be immobilized at any region on the capture medium upstream from the test site.

In certain embodiments, the test device includes a release medium comprising a detectable label and a first binding member reactive with a first epitope of FSH and a biotinylated capturable component comprising a second binding member reactive with a second epitope of FSH. According to such embodiments, when FSH is present in the sample, a complex is formed comprising the labeled conjugate, FSH, and the biotinylated capturable component. Such devices also include a capture medium including a test site having immobilized thereon a capture component comprising neutravidin, streptavidin, or the like. In one embodiment, the capture component comprises polymerized streptavidin, more preferably greater than 50% by weight of the polymerized streptavidin is at least about 100 kDa in size. In one embodiment, a scavenger component can be located downstream from the sample deposit and up to and including a region including the labeled conjugate. In another embodiment, such devices can include a scavenger component located downstream from a region including the labeled conjugate and up to and including a region including the biotinylated capturable component. In yet another embodiment, the scavenger component can be located at any region on the capture medium upstream from the test site.

In certain embodiments, the scavenger component that is reactive with FSH, a FSH-labeled conjugate complex, a biotinylated capturable component-FSH-labeled conjugate complex, or combinations thereof. For example, a device for detecting FSH can include a release medium formed of a first material and comprising a detectable label and a capture medium in fluid communication with the release medium and formed of a second, different material, the capture medium comprising a test site. Such an embodiment also includes a scavenger component that is reactive with FSH, a FSH-labeled conjugate complex, a biotinylated capturable component-FSH-labeled conjugate complex, or combinations thereof. The scavenger component can be located between the location of sample deposit and the test site, and can subtract the predetermined level of FSH in either liquid phase or through immobilizing it on the capture medium.

Preferably, the scavenger component is provided or striped onto the test device in a predetermined amount calibrated to subtract a predetermined level of FSH. Thus, any excess FSH above the predetermined amount subtracted from the sample by the scavenger will be bound by the labeled conjugate and detected at the test site.

According to various embodiments, the scavenger component or antibody can be located downstream from the deposit location of the liquid sample and up to and including a region including the labeled conjugate. In other embodiments, the scavenger antibody can be located between a region including the labeled conjugate and a region including the test site. Alternatively, the scavenger antibody can be located at any region on the release medium and at any region on the capture medium upstream from the test site.

Further embodiments of the present invention also include a control site or line downstream of the test site. The control site includes an antibody or an IgG binding protein (e.g., Protein A or Protein G) that is immobilized on the capture medium and that recognizes the labeled conjugate that binds with an epitope of FSH. Therefore, the result of a normal FSH level according to such a device will be displayed as one line (i.e., control site), whereas an elevated FSH level will be displayed as two lines (i.e., test site and control site). FIG. 9 illustrates a few locations on a test device where the scavenger component can be located. Although FIG. 9 illustrates an avidin-biotin device, the incorporation of a scavenging component and the positioning thereof is applicable to traditional lateral flow embodiments as well. FIG. 9, however, shows a test device 18 including a release medium 30 and a capture medium 32. Immobilized on the capture medium 32 are, respectively, the test site 34 and the control site 36. Also striped on the capture medium is a scavenger component 50 optionally located upstream of the test site 34. The release medium 30 includes a band 26 of labeled binding member, e.g., an antibody-metal sol, and a band 28 of capturable component e.g., antibody-biotin, releasably disposed on the release medium 30. As shown in FIG. 9, the test device can optionally include all or a portion of the scavenger component 54 positioned in the same band as the capturable component 28. FIG. 9 also shows that all or a portion of the scavenger component 58 can be striped upstream of the band 26 of labeled binding member.

Ovarian Reserve

In another aspect, the present invention provides a method for evaluating an individual's ovarian reserve, and thus fertility. Such methods, according to various embodiments, allow a user to evaluate their fertility in the confines of their own home or quickly in a physician's office or the like. In one embodiment, the method of determining ovarian reserve utilizes a test device according to the present invention. A liquid sample (e.g., urine) is applied to the sample deposit location. The sample deposit location is positioned upstream of the labeled conjugate and the biotinylated capturable component (in an avidin-biotin format). Preferably, the urine sample is a first morning urine collected from a pre- or peri-menopausal woman on Day 2, Day 3, Day 4, or Day 5 of her cycle (the first day is designated as the first day of spotting or bleeding). Most preferably, the sample is a first morning Day 3 urine sample. After depositing the liquid sample, the sample is allowed to wick downstream and pass the selected reagents deposited onto the test device for detecting a normal or elevated level of FSH. The user's ovarian reserve is determined based at least partially on the resulting color intensity or lack thereof at the test site. In certain embodiments, the capture medium of the test device includes a reference site having immobilized thereon a capture component comprising a binding member reactive with the labeled conjugate. In such embodiments, the color intensity of the reference site changes based on the amount of FSH present in the sample.

In one method, the test device includes a reference site so that the determination of ovarian reserve can be made based on a comparison of the resulting color intensities at the reference site and the test site. In such embodiments, when the color intensity of the test site is lighter than that of the reference site, the FSH level in the sample is deemed normal and below the predetermined level concentration.

In certain embodiments, the test device utilized includes a scavenger component that is reactive with FSH, a FSH-labeled conjugate complex, a biotinylated capturable component-FSH-labeled conjugate complex, or combinations thereof. In these embodiments, the scavenger component is provided in an amount to bind with a predetermined level of FSH. Thus, FSH above the predetermined level in the sample will bind to the labeled conjugate and ultimately be detected at the test site. In such an embodiment, the detection of any color at the test site indicates that the sample includes an FSH concentration above the predetermined level concentration. In this way, the results obtained while using a scavenging component are similar in nature to a pregnancy test kit.

Examples

Devices were produced with a biphasic medium containing Ahlstrom 989 (release medium) and Millipore 135 nitrocellulose membrane (capture medium). The release medium was striped with the gold colloid labeled anti-β FSH antibody (Medix Biochemica, anti-FSH 6602) at 30 OD and a biotinylated anti-α FSH antibody (Church & Dwight Co. Inc., anti-FSH 132) at 100 µg/mL; the nitrocellulose membrane was striped with neutravidin at 1.0 mg/L and a goat anti mouse IgG at (55-75 µg/mL). Under these experimental conditions, levels of FSH above the predetermined level will yield a test line that is equal to or darker than the reference line; therefore, test results are considered elevated for FSH. Prepared devices were tested with first morning urine samples collected from pre- and peri-menopausal women on Day 3 of the menstrual cycle. Clinical samples were characterized for FSH levels using a Siemens Immulite 1000 analyzer and corresponding FSH test kit, and the analyte concentrations were normalized utilizing the specific gravity values (Fisher Scientific Refractometer Cat#13-946-35) for each sample.

The visual test results of devices were compared to urinary FSH levels determined by Immulite 1000 with specific gravity corrections. The results show that devices can discriminate FSH levels indicative of the preset normal/elevated (see Table 2). For instance, the visual test results agreed with the levels determined by Immulite 1000 over 91% of the time. In only four (4) instances did the visual test indicate a normal FSH level while the Immulite 1000 reported boarder line values. It should be noted that the visual test results accurately identified all significantly elevated FSH levels.

TABLE 2

Clinical Evaluation of FSH Test with Day 3 Urine Samples from Pre- and Peri-Menopausal Women

| Sample ID | Cohort | Specific Gravity | Visual Test Result NB1643 Lot | Urine FSH (mIU/mL) | Urine FSH SG corrected* mIU/mL |
|---|---|---|---|---|---|
| 003 LSE | Pre-menopausal | 1.032 | T < R | 6 | 3 |
| 006 KCM | Pre-menopausal | 1.015 | T < R | 6 | 6 |
| 007 SHV | Pre-menopausal | 1.003 | T < R | 0.3 | 2 |
| 008 R-B | Pre-menopausal | 1.004 | T < R | 1 | 1 |
| 012 R-K | Pre-menopausal | 1.007 | T < R | 1 | 2 |
| 014 SLV | Pre-menopausal | 1.006 | T < R | 1 | 2 |
| 015 I-D | Pre-menopausal | 1.008 | T < R | 1 | 2 |
| 016 JMZ | Pre-menopausal | 1.012 | T < R | 6 | 8 |
| 018 JLC | Pre-menopausal | 1.012 | T < R | 10 | 13 |
| 019 CAM | Pre-menopausal | 1.034 | T < R | 16 | 8 |
| 020 JTR | Pre-menopausal | 1.023 | T < R | 11 | 8 |
| 021 LMB | Pre-menopausal | 1.008 | T < R | 2 | 4 |
| 022 ALF | Pre-menopausal | 1.017 | T < R | 2 | 2 |
| 023 SMF | Pre-menopausal | 1.023 | T < R | 8 | 5 |
| 024 CHN | Pre-menopausal | 1.012 | T < R | 1 | 1 |
| 025 LAM | Pre-menopausal | 1.032 | T < R | 17 | 8 |
| 027 AJB | Pre-menopausal | 1.022 | T < R | 8 | 6 |
| 028 M-C | Pre-menopausal | 1.020 | T < R | 9 | 7 |
| 029 M-S | Pre-menopausal | 1.027 | T < R | 9 | 5 |
| 030 AHB | Pre-menopausal | 1.008 | T < R | 1 | 3 |
| 031 DRP | Pre-menopausal | 1.022 | T < R | 4 | 3 |
| 032 S-B | Pre-menopausal | 1.036 | T = R | 65 | 27 |
| 033 RLK | Pre-menopausal | 1.023 | T < R | 7 | 4 |
| 034 A-G | Pre-menopausal | 1.026 | T < R | 11 | 7 |
| 035 S-R | Pre-menopausal | 1.009 | T < R | 4 | 7 |
| 001 LR | Peri-menopausal | 1.037 | T > R | 75 | 41 |
| 002 MIM | Peri-menopausal | 1.017 | T < R | 8 | 9 |
| 003 KM | Peri-menopausal | 1.011 | T > R | 27 | 48 |
| 006 LB | Peri-menopausal | 1.024 | T < R | 4 | 4 |
| 008 GF | Peri-menopausal | 1.009 | T < R | 3 | 6 |
| 009 MK | Peri-menopausal | 1.010 | T < R | 1 | 2 |
| 010 UM | Peri-menopausal | 1.007 | T > R | 15 | 41 |
| 011 IMW | Peri-menopausal | 1.032 | T < R | 22 | 14 |
| 012 RWW | Peri-menopausal | 1.018 | T < R | 6 | 7 |
| 013 AK | Peri-menopausal | 1.023 | T < R | 6 | 5 |
| 015 SDN | Peri-menopausal | 1.009 | T < R | 1 | 1 |
| 016 ELJ | Peri-menopausal | 1.025 | T < R | 19 | 15 |
| 017 LL | Peri-menopausal | 1.032 | T < R | 14 | 9 |
| 018 AML | Peri-menopausal | 1.029 | T < R | 4 | 3 |
| 019 LAR | Peri-menopausal | 1.018 | T < R | 4 | 5 |
| 020 PDK | Peri-menopausal | 1.022 | T < R | 11 | 10 |
| 021 TLB | Peri-menopausal | 1.015 | T < R | 4 | 6 |
| 022 SGG | Peri-menopausal | 1.008 | T < R | 2 | 5 |
| 025 SEA | Peri-menopausal | 1.017 | T = R | 14 | 16 |
| 026 KMS | Peri-menopausal | 1.016 | T < R | 2 | 2 |

*Miller et al. Methods for Normaliziing Hormone Concentrations, J. Clin. Chem. 50: 5, 924-232 (2004).
T < R: Test line intensity is lighter than reference line intensity (normal FSH)
T = R: Test line intensity is equal to reference line intensity (elevated FSH)
T > R: Test line intensity is greater than reference line intensity (elevated FSH)

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device for detecting Follicle Stimulating Hormone (FSH) present in a liquid sample at a concentration relative to a predetermined level, wherein the device comprises:
   A) a sample application member for receiving the liquid sample;
   B) a first portion comprising a labeled conjugate with a detectable label and a first binding member reactive with a first epitope of FSH; and
   C) a second portion comprising (i) a single test site having immobilized thereon a capture component capable of directly or indirectly binding with a second epitope of the FSH, the device further including a scavenger component in an amount sufficient to bind FSH present in the sample below the predetermined level, the scavenger component being located between the sample application member and the test site, such that a signal indicating binding of FSH at the test site only occurs when FSH is present in the liquid sample at a concentration above the predetermined level and no signal at the test site indicates any FSH in the liquid sample is present at a concentration below the predetermined level and (ii) a control site having immobilized thereon a capture component comprising a binding member that binds labeled conjugate.

2. The device of claim 1, wherein a normal FSH level is indicated by the presence of color only at the control site and an elevated FSH level is indicated by the presence of color both at the test site and the control site.

3. The device of claim 1, wherein the scavenger component is a component that is reactive with FSH, a FSH-labeled conjugate complex, a biotinylated capturable component-FSH-labeled conjugate complex, or combinations thereof.

* * * * *